United States Patent
Jamruszka-Lewis et al.

(10) Patent No.: US 9,572,300 B2
(45) Date of Patent: *Feb. 21, 2017

(54) METHODS OF TRANSFERRING PLANT EMBRYOS TO GERMINATION MEDIUM

(71) Applicant: WEYERHAEUSER NR COMPANY, Federal Way, WA (US)

(72) Inventors: Amy M. Jamruszka-Lewis, Sumner, WA (US); Robert A. Starr, Auburn, WA (US)

(73) Assignee: Weyerhaeuser NR Company, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/794,093

(22) Filed: Jul. 8, 2015

(65) Prior Publication Data

US 2015/0305248 A1 Oct. 29, 2015

Related U.S. Application Data

(63) Continuation of application No. 13/926,256, filed on Jun. 25, 2013, now Pat. No. 9,090,872.

(51) Int. Cl.
| | | |
|---|---|---|
| *C12N 5/00* | (2006.01) | |
| *C12N 5/02* | (2006.01) | |
| *C12N 5/04* | (2006.01) | |
| *A01G 1/00* | (2006.01) | |
| *A01H 4/00* | (2006.01) | |

(52) U.S. Cl.
CPC ............... *A01G 1/001* (2013.01); *A01H 4/005* (2013.01); *C12N 5/04* (2013.01)

(58) Field of Classification Search
CPC ............ C12N 5/04; A01G 1/001; A01H 4/005
USPC .......................................................... 435/422
See application file for complete search history.

(56) References Cited

U.S. PATENT DOCUMENTS

| | | |
|---|---|---|
| 4,957,866 A | 9/1990 | Gupta |
| 5,034,326 A | 7/1991 | Pullman |
| 5,036,007 A | 7/1991 | Gupta |
| 5,041,382 A | 8/1991 | Gupta |
| 5,236,841 A | 8/1993 | Gupta |
| 5,294,549 A | 3/1994 | Pullman |
| 5,482,857 A | 1/1996 | Gupta |
| 5,563,061 A | 10/1996 | Gupta |
| 5,564,224 A | 10/1996 | Carlson |
| 5,687,504 A | 11/1997 | Carlson |
| 5,701,699 A | 12/1997 | Carlson |
| 5,821,126 A | 10/1998 | Durzan |
| 6,119,395 A | 9/2000 | Hartle |
| 7,530,197 B2 | 5/2009 | Timmis |
| 7,610,155 B2 | 10/2009 | Timmis |
| 2007/0269096 A1 | 11/2007 | Timmis |

*Primary Examiner* — Annette Para
(74) *Attorney, Agent, or Firm* — Perkins Coie LLP

(57) ABSTRACT

Methods of transferring a plurality of plant somatic embryos to germination medium are provided.

20 Claims, No Drawings

METHODS OF TRANSFERRING PLANT EMBRYOS TO GERMINATION MEDIUM

CROSS-REFERENCE TO RELATED APPLICATION

This application is entitled to and claims the benefit of priority from U.S. patent application Ser. No. 13/926,256 filed Jun. 25, 2013, and titled "Methods of Transferring Plant Embryos to Germination Medium," the contents of which are incorporated herein by reference.

BACKGROUND

Modern silviculture often requires the planting of large numbers of genetically identical plants that have been selected to have advantageous properties. Production of new plants by sexual reproduction, which yields botanic seeds, is usually not feasible. Asexual propagation, via the culturing of somatic or zygotic embryos, has been shown for some species to yield large numbers of genetically identical embryos, each having the capacity to develop into a normal plant.

Somatic cloning is the process of creating genetically identical plants from plant tissue other than male and female gametes. In one approach to somatic cloning, plant tissue is cultured in an initiation medium that includes hormones, such as auxins and/or cytokinins, to initiate formation of embryogenic tissue, such as an embryogenic suspensor mass, that is capable of developing into somatic embryos. An embryogenic suspensor mass, or ESM, has the appearance of a whitish translucent mucilaginous mass and contains a plurality of early stage embryogenic tissue. The embryogenic tissue is further cultured in a multiplication medium that promotes multiplication and mass production of the embryogenic tissue. The embryogenic tissue is then cultured in a development medium that promotes development and maturation of cotyledonary somatic embryos that can, for example, subsequently be placed on germination medium to produce germinants, which in turn can be transferred to soil for further growth. Alternatively, the cotyledonary somatic embryos can be placed within manufactured seeds and sown in soil where they germinate to yield seedlings. Manufactured seeds are described, for example, in U.S. Pat. Nos. 5,564,224; 5,687,504; 5,701,699; and 6,119,395.

The typical somatic embryogenesis process is laborious and inefficient. For example, one of the more labor intensive and subjective steps in the embryogenesis process is the selective harvesting of individual embryos suitable for germination from development medium. At the end of the development period, the embryos may be present in a number of stages of maturity and development. Those that are most likely to successfully germinate into normal plants are preferentially selected using a number of visually evaluated screening criteria. Typically, a skilled technician evaluates the morphological features of each embryo, such as the embryo's size, shape (e.g., axial symmetry), cotyledon development, surface texture, color, and the like, and manually plucks desirable embryos with a pair of tweezers and transfers the selected embryos to germination medium. This is a highly skilled yet tedious job that is time consuming and expensive. Further, it poses a major production bottleneck when the ultimate desired output can be in the thousands of plants.

Automated methods for the harvesting of plant cotyledonary embryos from development medium have been developed, for example, as described in U.S. Pat. No. 7,530,197. At the end of the development phase, the embryos are typically attached to or imbedded in the embryogenic suspensor mass. It is important for subsequent normal germination to separate the embryos from the suspensor mass and from other embryos to yield individual embryos. This can be accomplished by a separation step in which plant embryos are physically separated from each other and the underlying embryogenic suspensor mass before further processing such as, for example, placement onto germination medium.

Separation can be accomplished by washing embryos off of a development medium using aqueous liquid, and then passing the embryos through a porous material, such as a sieve. During sieving, the embryos may be further sprayed with aqueous liquid to facilitate removal and washing away of any undesirable material, such as undersized embryos, tissues, and residual embryonal suspensor mass, through the holes of the porous material, and to sort the embryos according to size. Sorting according to size can be accomplished by using porous materials with various pore sizes. The mesh opening sizes of the sieve(s) can be selected so as to capture the desired sized embryos. The mesh opening sizes may vary in the range from about 500 microns to about 2400 microns. By adjusting the mesh opening size/shape of the one or more sieves, only those embryos within a desirable size/shape range are selected, resulting in a population comprising mostly of a plurality of individual embryos separated from each other and substantially free of suspensor tissue.

Although automated methods have been developed for removing embryos from development medium, and sorting the embryos according to size, technicians are still relied on to select those embryos having characteristics that improve the probability that the selected embryos will successfully germinate into plants; and then to hand-pluck the embryos from the porous material, and transfer the embryos to germination medium. The selection process is highly subjective, and the transferring of embryos to germination medium by hand remains a tedious, laborious, and ergonomically challenging process.

Efforts have been made to use instrumental image analysis for embryo selection to supplement or replace the visual evaluation performed by technicians. For example, an elaborate and complex classification method is disclosed in U.S. Publication No. 2007/0269096, which describes the classification of plant embryos by the application of classification algorithms to digitized images of plant embryos, and absorption, transmittance, or reflectance spectra of the embryos, to determine which embryos are likely to develop into germinants. Similarly, U.S. Pat. No. 7,610,155 describes using image and spectral data from known quality embryos to develop a classification model, using a classification algorithm, such as logistic regression (LR) analysis, to classify embryos as (i) embryos that likely will not germinate; (ii) embryos that may germinate with extra care; and (iii) embryos that will germinate with minimal care. The classification model is then applied to image and/or spectral data acquired from a plant embryo of unknown quality to determine the likelihood the embryo will develop into a germinant. Although determining the germination potential of embryos by classification modeling is a more objective process than selection of embryos by technicians, such methods involve the use of expensive instrumentation to collect the required images and data on each embryo, as well as extensive studies of embryos of known quality to develop the modeling system.

Thus, there exists a need for methods of transferring embryos en masse to germination medium that simplify the process, eliminate the step of determining germination potential of individual embryos, reduce the risk of contamination of the embryos, reduce labor and technician fatigue, reduce the risk of worker injury, and increase the production rate to achieve commercial scale.

The present disclosure describes methods of transferring plant somatic embryos en masse to germination medium.

SUMMARY

Methods of transferring plant somatic embryos to germination medium are provided. Each of the methods includes the steps of: (a) depositing a plurality of plant somatic embryos on a surface of a substrate, wherein the substrate has a top surface and a bottom surface; (b) inverting the substrate with the disposed plurality of plant somatic embryos over germination medium contained in a container such that the plurality of plant somatic embryos disposed on the top surface of the substrate are opposite to and facing a surface of the germination medium; and (c) applying a sufficient force to the bottom surface of the substrate such that the plurality of plant somatic embryos are dislodged from the substrate and fall onto the surface of the germination medium. Steps (b) and (c) of the methods can be performed manually or as part of an automated system. The methods also include subjecting the plurality of plant somatic embryos on germination medium to suitable environmental conditions for a period of time sufficient to promote germination of the plurality of plant somatic embryos.

DETAILED DESCRIPTION

As used herein, the term "embryogenic suspensor mass" (ESM) refers to early stage embryogenic cells in the process of multiplication by budding and cleavage.

As used herein, the term "embryogenic tissue" refers to an aggregate of tens to hundreds of embryogenic cells that form an embryogenic suspensor mass.

As used herein, the term "plant embryo" refers to a somatic plant embryo. Somatic plant embryos may be produced by culturing embryogenic tissue by standard methods under laboratory conditions in which the cells comprising the tissue are separated from one another and induced to develop into minute complete embryos. As used herein, "plant embryo" includes embryos at various stages of development.

As used herein, the term "cotyledonary embryo" refers to an embryo that possesses one or more cotyledons. Cotyledonary embryos have a well defined elongated bipolar structure with latent meristem with cotyledonary primordia at one end and a potential radicle at the opposite end. The cotyledonary structure frequently appears as a small "crown" at one end of the embryo.

As used herein the term "germinant" refers to an immature plant that possesses a well developed radicle and cotyledonary structure with a growing epicotyl, both readily apparent to the naked eye, and ready for planting in soil. For example, germinants typically have an epicotyl of about 10 mm or greater.

As used herein, the terms "separate" or "separation" refers to the process of separating cotyledonary embryos from attached embryogenic suspensor mass and sorting the embryos according to size.

As used herein, the terms "singulate" or "singulation" refers to the process of dispensing embryos on a substrate as individual, discrete embryos.

The somatic embryogenesis process is a process to develop plant embryos in vitro. Methods for producing plant somatic embryos are known in the art and have been previously described (see, e.g., U.S. Pat. Nos. 4,957,866; 5,034,326; 5,036,007; 5,041,382; 5,236,841; 5,294,549; 5,482,857; 5,563,061; and 5,821,126). Generally, the somatic embryogenesis process includes the steps of (1) initiation or induction, to initiate formation of embryogenic tissue, such as an embryogenic suspensor mass (ESM), which is a white mucilaginous mass that includes early stage embryos having a long, thin-walled suspensor associated with a small head with dense cytoplasm and large nuclei; (2) multiplication, sometimes referred to as maintenance, to multiply and mass produce embryogenic tissue; (3) development, to develop and form mature cotyledonary somatic embryos; and (4) post development steps such as separation, singulation, stratification, germination, placement into manufactured seeds, and transferring to soil for further growth and development.

The somatic embryogenesis process is labor intensive. Efforts have been made to automate and scale-up the process to facilitate the production of plant embryos in large scale, perhaps tens of thousands at a time. For example, the multiplication step may be carried out in a commercial-scale liquid bioreactor. At the end of the multiplication step, embryogenic tissue in the form of an embryogenic suspensor mass may be transferred to development medium for a period of time to develop into a plurality of cotyledonary embryos. At the end of the development period, the plurality of cotyledonary embryos are to various degrees attached to and embedded in suspensor tissue and residual underdeveloped ESM, together with incompletely developed embryos, abnormally formed embryos, undersized or oversized embryos, and other pieces of non-embryo plant material, and to other embryos. It is important for subsequent normal germination to separate each embryo from the suspensor mass and from other embryos to yield a plurality of individual embryos.

The plurality of individual embryos can be washed off from the development medium using aqueous liquid, such as water or an isotonic nutrient solution, and passed through a series of porous materials or sieves to sort the plurality of embryos into different sizes. During sieving, the plurality of embryos may be further sprayed with an aqueous liquid to facilitate removal and washing away of any undesirable material, such as undersized embryos, tissues, and residual ESM, through the holes of the sieves. The mesh opening sizes of the sieve(s) can be selected so as to capture the desired sized embryos. Typically, sieves with a mesh opening or pore size from about 500 microns to about 2400 microns are used. For example, mesh opening sizes of 500, 850, 1000, 1180, 1400, 1700, 2000, and 2400 microns can be used.

The plurality of plant somatic embryos removed from the development medium can be transferred from the sieves directly to germination medium. Alternatively, the plurality of embryos can be singulated into individual discrete embryos to facilitate the selection of suitable embryos for transferring to germination medium.

After an appropriate time on germination medium, the germinants are placed in a potting soil mixture for further growth. Typically many thousands of germinants are potted at once for clonal field tests.

In one aspect, the present disclosure provides methods of transferring a plurality of plant somatic embryos to germination medium. Each of the methods includes the steps of: (a) depositing a plurality of plant somatic embryos on a surface of a substrate, wherein the substrate has a top surface and a bottom surface; (b) inverting the substrate with the disposed plurality of plant somatic embryos over germination medium contained in a container such that the plurality of plant somatic embryos disposed on the top surface of the substrate are opposite to and facing a surface of the germination medium; and (c) applying a sufficient force to the bottom surface of the substrate such that the plurality of plant somatic embryos are dislodged from the substrate and fall onto the surface of the germination medium.

In some embodiments the substrate is a porous substrate. The substrate can be made of any material that is non-toxic to the embryos and that can withstand the force applied to dislodge the embryos. In some embodiments, the porous substrate is a metal substrate such as a sieve. In some embodiments, the porous substrate is mounted in a frame. Examples of useful porous substrates include membranes, nylon fiber, woven mesh (e.g., nylon, stainless steel or plastic), natural fibers (e.g. cotton), paper, and polymeric fibers. In one embodiment, the porous substrate is a polymeric membrane. In one embodiment, the porous substrate is a nylon membrane.

In some embodiments, the force is applied by striking the bottom surface of the substrate with one or more implements. The implement can be of any suitable size, shape, and material. For example, the implement can be a metal, plastic, or wooden spatula.

In some embodiments, steps (b) and (c) of the methods of the present disclosure are performed manually. For example, in one embodiment, a technician grasps a substrate, having disposed on its top surface a plurality of plant somatic embryos, with a tool, such as a hemostat, and inverts the substrate over germination medium contained in a container. The technician then applies sufficient force to the bottom surface of the substrate, by striking the bottom surface of the substrate one or more times with an implement, to dislodge the plurality of plant somatic embryos from the substrate such that the plurality of plant somatic embryos fall onto the surface of the germination medium. In the methods of the present disclosure, it is not important that the embryos land on the germination medium in any particular array or degree of separation from each other.

In some embodiments, steps (b) and (c) of the methods of the present disclosure are automated methods. In some embodiments, the substrate with the disposed plurality of plant somatic embryos is grasped by a robotic arm and inverted over the germination medium. In some embodiments, the force is automatically applied to the bottom surface of the substrate by one or more implements striking the bottom surface of the substrate. In some embodiments, a plurality of implements automatically strike the bottom surface of the substrate simultaneously. In some embodiments, a plurality of implements automatically strike the bottom surface of the substrate sequentially.

In some embodiments, the steps of the automated methods are performed in a sterile enclosure, such as a HEPA-filtered laminar flow chamber.

In one aspect, automated methods of transferring a plurality of plant somatic embryos to germination medium are provided. Each of the methods includes the steps of: (a) depositing a plurality of plant somatic embryos on a surface of a substrate, wherein the substrate has a top surface and a bottom surface; (b) transferring the substrate with the disposed plurality of plant somatic embryos into a first container; (c) using a robotic arm to remove the substrate with the disposed plurality of plant somatic embryos from the first container; (d) using the robotic arm to invert the substrate with the disposed plurality of plant somatic embryos over germination medium contained in a second container such that the plurality of plant somatic embryos disposed on the top surface of the substrate are opposite to and facing a surface of the germination medium; and (e) applying a force to the bottom surface of the substrate such that the plurality of plant somatic embryos are dislodged from the substrate and fall onto the surface of the germination medium.

Whether plant embryos are transferred to germination medium manually or automatically, the methods of the present disclosure further include the step of placing the container of germination medium and the disposed plurality of plant somatic embryos into a suitable environment for a period of time to promote germination of the embryos. The container of germination medium and the disposed plurality of plant somatic embryos can be placed in the dark for a period of about one to two weeks at a temperature from about 21° C.-27° C., followed by exposure to light for a period of from about five weeks to about twelve weeks, for example six weeks, seven weeks, eight weeks, nine weeks, ten weeks, eleven weeks, twelve weeks, or more than twelve weeks, up to about sixteen weeks, to form a plurality of germinants. The plurality of germinants can subsequently be planted in soil for development into plants. Alternatively, the plurality of germinants can be stored in water for a period of time before planting.

Plant embryos suitable for use in the methods of the invention can be from any plant species, such as dicotyledonous or monocotyledonous plants, gymnosperms, and the like. Conifer embryos are suitable for use in the methods of the invention and can be from any conifer species including, but not limited to, species within the family Pinaceae, and genera *Pinus, Picea, Tsuga, Pseudotsuga, Thuja, Juniperis, Larix,* and *Sequoia.*

In some embodiments, the plant somatic embryos are conifer somatic embryos. In some embodiments, the plant somatic embryos are Douglas-fir somatic embryos. In some embodiments, the plant somatic embryos are Loblolly pine somatic embryos.

Germination medium suitable for germination of a variety of species are known in the art. Germination media suitable for the germination of Douglas-fir (*Pseudotsuga menziesii*) and Loblolly pine (*Pinus taeda*) embryos are provided in Example 1.

The methods of the present disclosure provide a simple process to transfer plant somatic embryos to germination medium. The methods of the present disclosure eliminate the need to utilize skilled technicians and/or complex classification modeling to select plant somatic embryos that are likely to germinate, and therefore remove subjectivity from the process, and reduce the need to expend resources on worker training and/or on expensive instrumentation.

Furthermore, the methods of the present disclosure can produce a large number of germinants suitable for planting, while significantly increasing productivity, reducing labor costs, and reducing risk of injury to workers, when compared to the methods generally used in the art of selecting embryos according to certain criteria and hand-plucking and transferring the embryos to germination medium. For example, generally, it takes a skilled technician about 20 minutes to select and hand-pluck embryos from one substrate (referred to herein as an "s-frame") containing about 200 embryos, which is a processing rate of about 3 s-frames per hour (600 embryos).

Using the manual methods of the present disclosure, a technician can process about 6 s-frames in 10 minutes, which is a processing rate of about 36 s-frames per hour, resulting in about a more than 10 fold increase in productivity and efficiency. Although the manual method still involves some ergonomic stress, it is less than the stress involved in the hand-plucking method.

When the methods of the present disclosure are automated, about 36 s-frames per hour can be processed, but because minimal technician time is involved, the savings in labor costs is even more substantial than the manual method. Furthermore, ergonomic stress is virtually eliminated with the automated method, thereby reducing the costs associated with repetitive motion and other injuries incurred by workers using the hand-plucking or the manual method.

The results achieved by the methods of the disclosure, as illustrated in the Examples below, are surprising because it has been previously thought that it is necessary to use certain criteria to select suitable embryos, and to treat the embryos gingerly, in order to achieve substantial numbers of germinants suitable for planting. Contrary to conventional thinking, applicants have found that a suitable number of germinants can be produced without using embryo selection criteria, and that the embryos can withstand a certain amount of physical stress. The methods of the disclosure thus enable the production of germinants at commercial scale, while significantly reducing costs, and increasing productivity and worker well-being.

The following examples are provided for the purpose of illustrating, not limiting, the present disclosure.

EXAMPLES

Example 1

This example provides the components of suitable germination medium for use in the methods of the present disclosure. Table 1 provides an exemplary medium for the germination of Douglas fir or Loblolly pine somatic embryos.

TABLE 1

| Germination Media | |
|---|---|
| Constituent | Concentration, mg/L |
| $NH_4NO_3$ | 206.3 |
| $KNO_3$ | 1170.0 |
| $CaCl_2 \cdot 2H_2O$ | 220.0 |
| $KH_2PO_4$ | 85.0 |
| $MgSO_4 \cdot 7H_2O$ | 185.0 |
| $MnSO_4 \cdot H_2O$ | 8.45 |
| $ZnSO_4 \cdot 7H_2O$ | 4.30 |
| $CuSO_4 \cdot 5H_2O$ | 0.013 |
| $FeSO_4 \cdot 7H_2O$ | 13.93 |
| $Na_2EDTA$ | 18.63 |
| $H_3BO_3$ | 3.10 |
| $NaMoO_4 \cdot 2H_2O$ | 0.125 |
| $CoCl_2 \cdot 6H_2O$ | 0.0125 |
| KI | 0.42 |
| myo-Inositol | 100.0 |
| Thiamine•HCL | 1.00 |
| Nicotinic acid | 0.50 |
| Pyridoxine•HCL | 0.50 |
| Glycine | 2.00 |
| Sucrose | 20,000 |
| pH | 5.7 |
| Activated charcoal | 2500 |
| Tissue culture agar | 8000 |

Example 2

This example illustrates the results obtained when a plurality of Loblolly pine embryos were transferred en masse to germination medium using an embodiment of the present disclosure.

Developed embryos and embryogenic matter were substantially separated from embryogenic suspensor mass, sorted according to size, and deposited on nylon porous substrates mounted in frames (referred to herein as "s-frames"). The developed embryos and/or embryogenic matter disposed on s-frames were placed in a high relative humidity environment (98%) for 2-4 weeks and then transferred to germination medium, as described below.

Each s-frame contained approximately 169 "objects" per frame. As used herein, "objects" refers collectively to developed intact embryos, as well as broken off pieces of cotyledon, pieces of residual ESM, partially developed embryos, etc.

Procedure 1. Control. For each batch, about forty-two complete, intact developed embryos were hand-selected by a technician from an s-frame and transferred to germination medium using tweezer tools.

Procedure 2. A technician used a hemostat to grasp an edge of an s-frame having objects disposed on the top surface, inverted the s-frame over semi-solid germination medium so that the objects were facing the germination medium, and applied force to the bottom surface of the s-frame using a spatula, thereby transferring objects en masse to the surface of the germination medium.

Results

In both Procedures 1 and 2, lids were placed on the boxes containing germination medium and disposed embryos/objects, and the boxes were wrapped and sealed, and placed in the dark for one week, followed by a period of five weeks in light. Germinants resulting from each procedure were assessed after 6 weeks, and the number of germinants resulting from the embryos per s-frame were counted. The results are set forth in Table 3 below.

TABLE 2

| Number of germinants per s-frame. | | | |
|---|---|---|---|
| Batch | Genotype | No. Germinants Procedure 1 | No. Germinants Procedure 2 |
| 1-a | A | 32 | 12 |
| 1-b | A | 48 | 15 |
| 2-a | B | 20 | 5 |
| 2-b | B | 12 | 5 |
| 2-c | B | 24 | 0 |
| 3-a | B | 12 | 24 |
| 3-b | B | 28 | 15 |
| 3-c | B | 8 | 3 |
| 3-d | C | 0 | 0 |
| 3-e | C | 0 | 1 |
| 3-f | C | 0 | 1 |
| 4-a | D | 16 | 25 (per 2 s-frames combined) |
| 4-b | D | 16 | |

TABLE 2-continued

Number of germinants per s-frame.

| Batch | Genotype | No. Germinants Procedure 1 | No. Germinants Procedure 2 |
|---|---|---|---|
| 4-c | D | 28 | 47 (per 2 s-frames combined) |
| 4-d | D | 8 | |
| 5 | E | 0 | 1 |

Discussion

In some batches, more germinants resulted when the hand-plucked method was used to transfer embryos to germination medium (Procedure 1). However in other batches, more germinants resulted when an exemplary embodiment of the methods of the present disclosure were used to transfer embryos to germination medium (Procedure 2). See for examples, Batches 3-a, 3-e, 3-f, combined 4-c and 4-d, and 5. These results demonstrate that an acceptable number of germinants result when embryos are transferred en masse to germination medium using the methods of the present disclosure. Furthermore, and importantly, the savings in time, labor, and efficiencies were substantial when Procedure 2 was used compared to Procedure 1.

Example 3

This example illustrates the results obtained when a plurality of Loblolly pine embryos were transferred en masse to germination medium using an embodiment of the present disclosure.

Developed pine embryos and embryogenic matter were substantially separated from embryogenic suspensor mass, sorted according to size, and deposited on s-frames. The developed embryos and/or embryogenic matter disposed on s-frames were placed in a high relative humidity environment (98%) for 2-4 weeks, and then transferred to germination medium, using Procedure 1 or Procedure 2, as described in Example 1. Each procedure included four genotypes and one batch of each genotype.

After a six-week germination period, the number of germinants was assessed and the results were analyzed as described below.

The number of germinants resulting from each procedure were statistically analyzed with generalized linear models using a logit link and the mean was determined for each procedure. In the case of Procedure 1, the "mean" represents the number of germinants resulting from the number of embryos hand-plucked from a batch and transferred to germination medium. In the case of Procedure 2, the "mean" represents the number of germinants resulting from the number of objects per frame transferred to germination medium.

The means were transformed back to the natural scale and pairwise comparisons between Procedure 1 and Procedure 2 were made using the Fisher's LSD multiple comparison method.

Results

The results are set forth in Table 3 below. Lower and Upper are the lower and upper 90% confidence limits, respectively, for each mean. The column "Test at p=0.10" summarizes test results comparing means. Means with the same letter are not statistically different at p=0.10.

TABLE 3

| Procedure | Estimate | Lower | Upper | Test at p = 0.10 |
|---|---|---|---|---|
| 1 | 0.070 | 0.048 | 0.099 | a |
| 2 | 0.069 | 0.050 | 0.095 | a |

No statistical difference was found in the number of germinants resulting from Procedure 1 when compared to Procedure 2. These results indicate that the methods of the present disclosure can be used to transfer a plurality of embryos en masse to germination medium without adversely affecting the embryos.

Discussion

The results from Example 3 illustrate that transferring embryos/objects en masse to germination medium does not significantly reduce the number of germinants produced, and therefore the methods of the present disclosure provide a viable alternative to using the labor intensive and ergonomically taxing hand-plucking method of Procedure 1.

While embodiments of the methods of the present disclosure have been illustrated and described, it will be appreciated that various changes can be made therein without departing from the spirit and scope of the invention.

The invention claimed is:

1. A method of transferring genetic plant tissue disposed on a first surface of a substrate, comprising:
    inverting the substrate over germination medium so that the surface of the substrate is facing a surface of the germination medium; and
    applying a force to a second surface of the substrate so that the genetic plant tissue is caused to dislodge from the substrate and fall onto the surface of the germination medium.

2. The method of claim 1, further comprising placing the genetic plant tissue disposed on the surface of the substrate in a high relative humidity environment for a certain period of time before being transferred to the germination medium.

3. The method of claim 2 comprising placing the genetic plant tissue disposed on the surface of the substrate in an environment with about 98% humidity for a period of about two to four weeks.

4. The method of claim 1 wherein the inverting a substrate is performed by a robotic ann.

5. The method of claim 1 wherein the germination medium is semi-solid and contained in a container.

6. The method of claim 5 comprising covering the container with a lid after applying the force to the second surface of the substrate.

7. The method of claim 1 wherein the substrate comprises at least one of a membrane, nylon fiber, woven mesh, natural fiber, paper, or polymeric fiber.

8. The method of claim 1 wherein the force is applied automatically by one or more implements striking the second surface of the substrate.

9. The method of claim 8 wherein the one or more implements automatically strike the second surface of the substrate simultaneously or sequentially.

10. The method of claim 1 further comprising placing the genetic plant tissue disposed on the germination medium in the dark for a period of time, followed by exposing the genetic plant tissue to light for another period of time.

11. The method of claim 1 wherein the genetic plant tissue comprises one or more plant embryos.

12. A method, comprising:
grasping a substrate with a robotic arm, the substrate having embryonic tissues disposed on a surface;
inverting the substrate with the robotic arm over a germination medium so that the surface of the substrate is facing toward a surface of the germination medium; and
applying a force to the substrate so that the embryonic tissue is caused to fall onto the surface of the germination medium.

13. The method of claim 12 wherein the applying a force comprises striking a second surface of the substrate simultaneously or sequentially with one or more implements.

14. The method of claim 12 wherein the germination medium is semi-solid and contained in a container.

15. The method of claim 14 comprising covering the container with a lid after applying the force to the substrate.

16. The method of claim 12 wherein the substrate comprises at least one of a membrane, nylon fiber, woven mesh, natural fiber, paper, or polymeric fiber.

17. The method of claim 12 further comprising placing the embryonic tissues disposed on the germination medium in the dark for a period of time, followed by exposing the genetic plant tissue to light for another period of time.

18. The method of claim 12 wherein the embryonic tissues comprises one or more plant embryos.

19. The method of claim 18, further comprising placing the one or more plant embryos disposed on the surface of the substrate in a high relative humidity environment for a certain period of time before being transferred to the germination medium.

20. The method of claim 19 comprising placing the one or more plant embryos disposed on the surface of the substrate in an environment with about 98% humidity for a period of about two to four weeks.

* * * * *